United States Patent
Khomchenko

(10) Patent No.: US 7,452,355 B2
(45) Date of Patent: Nov. 18, 2008

(54) METHOD OF LASER COAGULATION OF BLOOD VESSELS

(76) Inventor: Vladimir Valentinovich Khomchenko, ul. Tushinskaya, 12-28, Moscow 123362 (RU)

( * ) Notice: Subject to any disclaimer, the term of this patent is extended or adjusted under 35 U.S.C. 154(b) by 0 days.

(21) Appl. No.: 10/499,610

(22) PCT Filed: Jul. 25, 2001

(86) PCT No.: PCT/RU01/00304

§ 371 (c)(1), (2), (4) Date: Mar. 24, 2005

(87) PCT Pub. No.: WO02/22035

PCT Pub. Date: Mar. 21, 2002

(65) Prior Publication Data

US 2005/0203491 A1 Sep. 15, 2005

(30) Foreign Application Priority Data

Sep. 12, 2000 (RU) .............................. 2000123241

(51) Int. Cl.
*A61B 18/20* (2006.01)
(52) U.S. Cl. .......................................... 606/3; 128/898
(58) Field of Classification Search ................. 128/898; 606/3–10
See application file for complete search history.

(56) References Cited

U.S. PATENT DOCUMENTS

| 5,344,418 | A | * | 9/1994 | Ghaffari | 606/9 |
| 5,345,457 | A | * | 9/1994 | Zenzie et al. | 372/22 |
| 5,595,568 | A | * | 1/1997 | Anderson et al. | 606/9 |
| 5,755,751 | A | * | 5/1998 | Eckhouse | 607/88 |
| 5,776,175 | A | * | 7/1998 | Eckhouse et al. | 607/100 |
| RE36,634 | E | * | 3/2000 | Ghaffari | 606/9 |
| 6,267,779 | B1 | * | 7/2001 | Gerdes | 607/89 |
| 6,514,243 | B1 | * | 2/2003 | Eckhouse et al. | 606/9 |
| 6,569,156 | B1 | * | 5/2003 | Tankovich et al. | 606/10 |
| 6,613,042 | B1 | * | 9/2003 | Tankovich et al. | 606/10 |
| 6,766,187 | B1 | * | 7/2004 | Black et al. | 600/473 |
| 2004/0225339 | A1 | * | 11/2004 | Yaroslavsky et al. | 607/77 |

FOREIGN PATENT DOCUMENTS

| RU | 2104068 C1 | 2/1998 |
| RU | 2114585 C1 | 7/1998 |
| RU | 2144342 C1 | 1/2000 |

* cited by examiner

*Primary Examiner*—Henry M Johnson, III
(74) *Attorney, Agent, or Firm*—Weingarten, Schurgin, Gagnebin & Lebovici LLP

(57) ABSTRACT

The invention provides laser methods for treatment and prophylaxis of hemangioma, phlebectasia and other vascular lesions. The methods increase the effectiveness of blood vessel coagulation while diminishing the probability of trauma to surrounding soft tissue. Blood vessels are subjected to a pulse radiation having a wavelength of 500-600 nm and an energy density up to 10 Joules/cm$^2$ for not more than 10 ms, and simultaneously are subjected to at least one more radiation of wavelength in the range of 800-1400 nm and an energy density not exceeding 100 Joules/cm$^2$. The energy density and influence duration for the pulse radiations depend upon the size of the blood vessels to be coagulated. The pulse radiations may be applied either by single pulses with a duration of not more than 10 ms, or by a packet of several nanosecond pulses lasting not more than 10 ms.

7 Claims, No Drawings

METHOD OF LASER COAGULATION OF BLOOD VESSELS

TECHNICAL FIELD

The subject invention relates to laser medicine, in particular to dermatology, and can be used for medical treatment of hemangioma, treatment and prophylaxis of phlebectasia and other vascular lesions.

BACKGROUND

A method of laser coagulation of vessels by argon laser, radiation wavelength 488-514 nm is known ["Laser surg. Med.", 1992, vol. 12, pp. 246-253. "Applied laser medicine". Edited by H. P. Berlien, G. Y. Muller, pp. 326-327, 1997].

The medical effect in laser coagulation of vessels by argon laser, radiation wavelength 488-514 nm is based on the fact that argon laser radiation is well absorbed by hemoglobin, leading to temperature increase inside the blood vessels resulting in coagulation of the blood vessels.

But the radiation wavelength with laser coagulation of vessels by argon laser, radiation wavelength 488-514 nm is not able to penetrate deep into blood vessels, hence the method cannot be used for the coagulation of big vessels. Moreover, the argon laser radiation is also well absorbed by other skin constituents resulting in-the overheating of surrounding tissue and diminishes the medical effect even in coagulation of small vessels.

An additional method of blood vessels coagulation involves use of YAG:Nd laser operating in the mode of the second harmonic generation is also known in the art [U.S. Pat. No. 5,558,667, publication date 24 Sep. 1996, "Method and apparatus for treating vascular lesions".

YAG:Nd laser radiation with the wavelength of 532 nm, pulse duration of 0.5-10.0 ms and energy density of 10-20 Joules/cm$^2$ is also well absorbed by hemoglobin thereby allowing coagulation of small blood vessels. The disadvantage of the YAG:Nd laser radiation method lies in the fact that beside hemoglobin other constituents of soft tissue also absorb the radiation and the skin penetration deepness is not sufficient to coagulate the vessels without causing damage of the surrounding soft tissue.

An additional method for coagulation blood vessels involves use of dye laser radiation by pulses with the wavelength of 585 nm [Treatment of Vascular Lesions in Pigmented Skin with the Pulsed Dye Laser, "Laser surg. Med.", 1992, suppl. 4, pp. 65-74].

Such wavelength (e.g., 585 nm) allows deeper penetration into soft tissue at the expense of lesser absorption by various skin constituents. The absorption effectiveness of radiation with a 585 nm wavelength by hemoglobin is less than that of the argon and the second harmonic YAG:Nd lasers, though it is compensated that the radiation penetrates deeper inside the vessel causing blood coagulation in greater volumes. Owing to this fact, methods using radiation with a 585 nm wavelength allows coagulation of bigger vessels. However, to effectively heat the whole vessel volume it is necessary to use greater energies so as to avoid partial blood coagulation, which will not provide sufficient vessel walls heating and may cause displacement of the coagulated blood portion during blood circulation. In addition, the use of high-energy radiation in the given wavelength range provokes substantial overheating of the surrounding tissue, which may result in irreversible changes in them.

DETAILED DESCRIPTION

The object of the invention is to solve the problem of increasing the effectiveness of blood vessels coagulation while diminishing the probability of causing traumatosis of the surrounding soft tissue.

The assigned problem is solved by exposure of blood vessels to a pulse radiation with a wavelength of 500-600 nm, energy density up to 10 Joules/cm$^2$ during not more than 10 ms. Simultaneously the same blood vessels are exposed to at least one more additional pulse radiation with wavelength in the range of 800-1400 nm and energy density up to 100 Joules/cm$^2$.

The energy density and the influence duration are chosen depending upon the size of the vessel to be coagulated. The radiation may be applied either by single pulses during not more than 10 ms, or by a packet of several nanosecond pulses the duration of which does not exceed 10 ms.

The subject method is based on simultaneous influence of radiations with different wavelengths each of which separately cannot result in effective blood vessel coagulation. The radiation is applied either by way of a single pulse with a duration from hundreds of microseconds to tens of milliseconds, or by way of a pulse packet of nanosecond duration, in such case the packet duration should not exceed 10 milliseconds. The additional radiation wavelength range is chosen taking into account the condition of the poor absorption of skin constituents, i.e. deep penetration of the radiation into soft tissue.

A Comparison of the methods of the present invention with methods of the prior art reveals the following distinguishing features:

The methods of the present invention provide at least one more additional radiation with another wavelength for blood vessel coagulation;
  both radiations influence the vessel to be coagulated simultaneously;
  the additional radiation wavelength is chosen taking into account the condition of its deep penetration into the skin soft tissue;
  coagulation of the blood vessel is achieved with either single pulses, or a packet of nanosecond pulses with corresponding duration and energy density.

All of the aforesaid distinguishing features of the present invention allow it to be classified as "New in the Art."

Despite the fact that methods of laser coagulation of blood vessels are known in science and medical practice the methods of the present invention provide a new result. Previous methods of laser coagulation fail to take into account the effect of the spectrum absorption variation of the vessel being coagulated. In the claimed for method the coagulation process is effected by at least two simultaneous radiations with different wavelengths, the first of which creates inside the vessel separate zones of coagulated blood (e.g., the absorption centers for the radiation), and the second of which effects heating of the absorption centers accompanied by subsequent coagulation of the whole blood vessel.

The first The first radiation is provided with a wavelength in the range from 500 to 600 nm. A radiation with a wavelength in the range from 500 to 600 nm is effectively absorbed by hemoglobin and under the influence of this radiation the coagulation of blood portions takes place. In addition, as this radiation cannot penetrate deep into blood vessels, the coagulation centers are situated in the zone directly bordering the vessel's walls which contributes to their effective heating and coagulation. Under the influence of the additional radiation the temperature of the coagulated blood portions increases and the heat is transmitted to the non-coagulated blood portions causing their heating and the vessel's coagulation.

Moreover, the absorption spectrum of coagulated blood allows use of an additional radiation in the wavelength range from 800 to 1400 nm which is little absorbed by the skin and non-coagulated vessel's zones and, as a result, reduces the heating of surrounding soft tissue.

The influence on the vessel to be coagulated by simultaneous radiations with different wavelengths results in an increase in coagulation effectiveness and a reduction in traumatosis of surrounding tissue.

As prolonged exposure of skin to the wavelength of the first radiation is may cause undesirable overheating, the time of the first radiation influence may be minimized and/or its intensity may be decreased towards the end of influence time. The radiation with the second wavelength in its turn is formed with inverse relationship, i.e. its intensity may be increased towards the end of influence period. By controlling the pulses duration and the radiation intensity it is possible to effect selective regulation of temperature in large blood vessels at minimum thermal heating of surrounding soft tissue.

EXAMPLE

The biological tissue is influenced by a laser radiation either by way of two compatible in time pulses, or by way of two packets of nanosecond pulses. To generate radiation with wavelengths in the ranges of 500-600 nm and 800-1400 nm it is possible to use YAG:Nd laser with the active modulation of the Q-factor and generation of the second harmonic. In this case the radiation intensity of the second harmonic will be in non-linear dependence on the intensity of the first one.

Under the radiation influence with the wavelength of 532 nm, energy density of 10 Joules/cm$^2$ with duration of 5 ms and spot diameter of 1 mm in the biological tissue—blood vessel a partial coagulation takes place and zones of coagulated blood are formed. Simultaneously the same vessel is being influenced by radiation with the wavelength of 1064 nm at energy density of 70 Joules/cm$^2$ during 10 ms and spot diameter of 1 mm. This radiation influences the coagulated zones in the vessel and effects complete vessel coagulation not causing damage to surrounding soft tissue.

The invention claimed is:

1. A method of laser coagulation of blood vessels comprising the steps of:
   simultaneously subjecting said blood vessels to a first pulse radiation and a second pulse radiation,
   wherein said first pulse radiation has a wavelength of 500-600 nm, and an energy density of not more than 10 Joules/cm$^2$, wherein the duration of said first pulse radiation is less than 10 ms,
   wherein said second pulse radiation has a wavelength in the range of 800-1400 nm, and an energy density of not more than 100 Joules/cm$^2$.

2. The method of claim 1, wherein said energy density and said duration for said first pulse radiation and said second pulse radiation are chosen depending upon the size of the blood vessels to be coagulated.

3. The method of claim 1, wherein said first pulse radiation and said second pulse radiation are applied in single pulses for a duration not more than 10 ms.

4. The method of claim 1, wherein said first pulse radiation and said second pulse radiation are applied by way of a packet of several nanosecond pulses for a duration of not more than 10 ms.

5. The method of claim 1, wherein the energy density of the first pulse radiation is reduced at the end of the first pulse radiation influence period.

6. The method of claim 1, wherein the energy density of the second pulse radiation is increased at the end of the second pulse radiation influence period.

7. The method of claim 1, wherein the energy density of the first pulse radiation is reduced at the end of the first pulse radiation influence period and the energy density of the second pulse radiation is increased at the end of the second pulse radiation influence period.

* * * * *